United States Patent [19]

Daines et al.

[11] Patent Number: 6,100,267

[45] Date of Patent: Aug. 8, 2000

[54] QUINOLINE- AND NAPHTHALENECARBOXAMIDES, PHARMACEUTICAL COMPOSITIONS AND METHODS OF INHIBITING CALPAIN

[75] Inventors: Robert A Daines, Lansdale; William D Kingsbury, Phoenixville; Israil Pendrak, Norristown; John P Mallamo, Glenmoore, all of Pa.

[73] Assignees: SmithKline Beecham Corporation, Philadelphia; Cephalon, Inc., West Chester, both of Pa.

[21] Appl. No.: 09/380,318

[22] PCT Filed: Mar. 13, 1998

[86] PCT No.: PCT/US98/04874

§ 371 Date: Aug. 30, 1999

§ 102(e) Date: Aug. 30, 1999

Related U.S. Application Data

[60] Provisional application No. 60/040,583, Mar. 14, 1997.

[51] Int. Cl.[7] .................. A61K 31/495; A61K 31/44; C07D 213/53; C07D 421/00

[52] U.S. Cl. ............... 514/255; 514/682; 514/357; 514/255; 546/329; 546/268.1

[58] Field of Search ............... 568/306; 514/682, 514/357, 255, 617, 619, 546, 551, 616; 544/338, 363; 546/329, 268.1; 564/160, 155, 163, 161, 168, 244; 560/126

[56] References Cited

U.S. PATENT DOCUMENTS 4,970,214 11/1990 Murase et al. ................... 514/311

FOREIGN PATENT DOCUMENTS

WO95/32948 12/1995 WIPO .

*Primary Examiner*—Zinna Northington Davis
*Assistant Examiner*—Binta Robinson
*Attorney, Agent, or Firm*—Zoltan Kerekes; Stephen Venetianer; Charles M. Kinzig

[57] ABSTRACT

Pharmaceutical compositions and methods of inhibiting calpain using novel quinoline- or naphthatenecarboxamides are disclosed.

23 Claims, No Drawings

QUINOLINE- AND NAPHTHALENECARBOXAMIDES, PHARMACEUTICAL COMPOSITIONS AND METHODS OF INHIBITING CALPAIN

This application is a 371 of PCT/US98/04874 filed Mar. 13, 1998 which claims the benefit of priority to this provisional application, 60/040,583, filed Mar. 14, 1997.

SUMMARY OF THE INVENTION

This invention relates to novel chemical compounds which are quinoline- or aphthalenecarboxamides. The claimed pharmaceutical compositions and methods use those compounds as active ingredients to inhibit calpain and thus are useful in the treatment of, for example, neurodegenerative disorders, strokes and traumatic brain injury.

BACKGROUND OF THE INVENTION

Calpains are calcium—dependent cysteine proteases present in a variety of tissues and cells. Excessive activation of calpain provides a molecular link between ischaemia or injury induced by increases in intraneuronal calcium and pathological neuronal degeneration. If the elevated calcium levels are left uncontrolled, serious structural damage to neurons may result. Recent research has suggested that calpain activation may represent a final common pathway in many types of brain damage. Selective inhibition of calpain would, therefore, be an attractive therapeutic approach in the treatment of neurodegenerative diseases. Exemplary of these diseases would be myocardial ischaemia, cerebral ischaemia, muscular dystrophy, stroke, Alzheimer's disease, or traumatic brain injury. The compounds of this invention may also be useful in the treatment of cataracts and platelet aggregation.

DETAILED DESCRIPTION OF THE INVENTION

The compounds which are the active ingredients of the pharmaceutical compositions and methods of this invention are represented by the following formula:

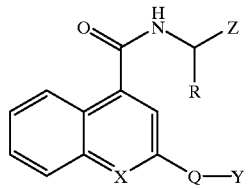

Formula I in which:
X is CH or N;
R is $CH_2Ph$, $-(CH_2)_3CH_2NR_1R_3$, $CH_2CH(CH_3)_2$ or $CH_2PhOR_2$;
$R_1$ is $COOCH_2Ph$, $SO_2CH_3$, $SO_2aryl$, $COOCH_{2pyridyl}$ (or substituted pyridyl);
$R_2$ is H, $CH_3$, $CH_2Ph$ or $CH_{2pyridyl}$;
$R_3$ is H, $CH_3$ or lower alkyl;
Z is CHO, $COCH_2F$, COCOOH, COCOOalkyl, COCONHalkyl, $COCO(CH_2)_n$aryl, COCONHCH(R)COOH or $COCH_2O$—(3-phenylisoxazol-5-yl);
n is 1 to 6;

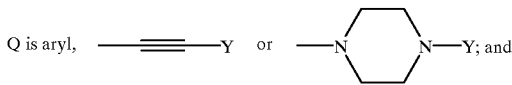

Y=absent, phenyl, substituted phenyl, pyridyl or substituted pyridyl,
or a pharmaceutically acceptable salt thereof.

Preferred compounds are those where the stereochemistry at the R group corresponds to that of the naturally occurring amino acids. Also preferred are those compounds where X is N, Z is CHO and R is $CH_2Ph$ or $-(CH_2)_3CH_2NR_1R_3$.

The following preferred compounds are representative of the compounds of the invention:

(S)-N-(1-formyl-2-phenylethyl)-2-phenyl-4-quinolinecarboxamide
(S)-2-(4-chlorophenyl)-N-(1-formyl-2-phenylethyl)-4-quinolinecarboxarmide
(S)-2-[1,1'-biphenyl]-4-yl-N-(1-formyl-2-phenylethyl)-4-quinolinecarboxamide
(S)-2-(1-adamantyl)-N-(1-formyl-2-phenylethyl)-4-quinolinecarboxamide
(S)-N-(1-formyl-2-phenylethyl)-2-(4-phenoxyphenyl)4-quinolinecarboxamide
(S)-2-[1,1'-biphenyl]-2-yl-N-(1-formyl-2-phenylethyl)-4-quinolinecarboxamide
(S)-N-(1-formyl-2-phenylethyl)-2-(2-pyridinylethynyl)-4-quinolinecarboxamide
(S)-N-(1-formyl-2-phenylethyl)-2-(4-phenyl-1-piperazinyl)-4-quinolinecarboxamide
(S)-N-[1-formyl-2-phenylethyl]-2-[(3-(pyridinyl)-4-phenyl]-4-quinolinecarboxamide
(S)-N-[1-formyl-5-[(phenylsulfonyl)amino]pentyl]-2-phenyl-4-quinolinecarboxamide
(S)-N-[1-formyl-5-[N'-(carbo-4-pyridinemethyloxy)pentyl]-2-[phenyl-]4-quinoline-carboxamide
(S)-N-(1-formyl-2-phenylethyl)-2-(phenylethynyl)-4-quinolinecarboxamide
N-[3-(n-butylamino)-2,3-dioxo-1-(phenylmethyl)]-2-(phenylethynyl)-4-quinoline-carboxamide.

Compounds of Formula I where X is N are prepared by the methods described in Schemes 1–4.

Scheme 1

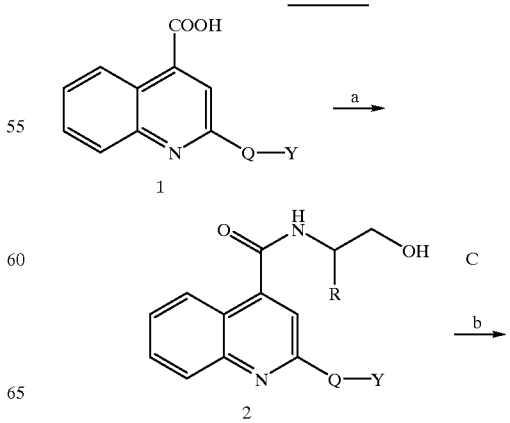

3
-continued

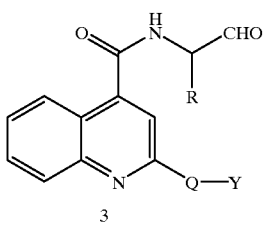

a) (S)-(-)-2-amino-3-phenyl-1-propanol, BOP, triethylamine, CH₂Cl₂;
b) Dess-Martin reagent, CH₂Cl₂

The 2-substituted quinolines 1 where Q-Y is phenyl or para-biphenyl are available from Aldrich Chemical Company. 1 is converted to the amide alcohol 2 by standard coupling conditions [(S)-(-)-2-amino-3-phenyl-1-propanol, benzotriazol-1-yloxytris(dimethylamino)-phosphoniumhexafluorophosphate (BOP), triethylamine, methylene chloride)]. The amide alcohol may be purified by silica chromatography. Oxidation of 2 (the Dess-Martin reagent in methylene chloride is prefered, but not limiting) affords the aldehyde 3. This procedure can be repeated with a wide variety of 2-substituted quinoline-4carboxylates and with a wide variety of amino alcohol derivatives. Those derived from the naturally occurring amino acids are preferred.

Compounds of Formula I wherein the quinoline containing the desired substituent at C-2 is not commercially available are prepared by the methods described in Schemes 2–4.

Scheme 2

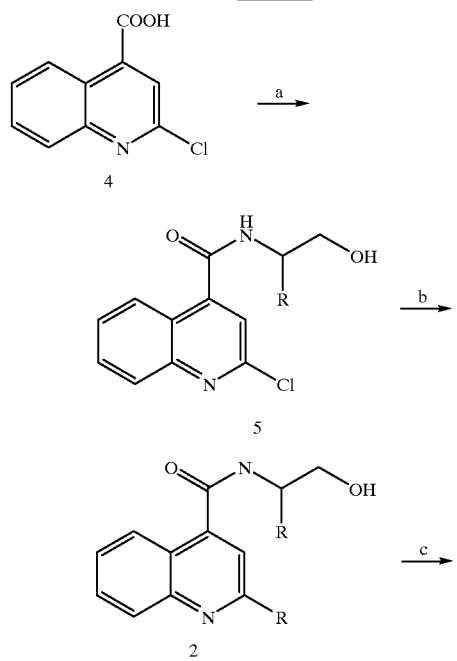

4
-continued

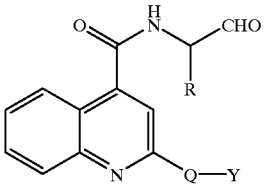

a) (S)-(-)-2-amino-3-phenyl-1-propanol, BOP, triethylamine, CH₂Cl₂;
b) RPd⁰;
c) Dess-Martin reagent, CH₂Cl₂

2-Chloroquinoline-4-carboxylic acid, 4, is available from ICN Chemical Company. 4 is converted to the amide alcohol 5 by standard coupling conditions as in Scheme 1 [(S)-(-)-2-amino-3-phenyl-1-propanol, benzotriazol-1-yloxytris(dimethylamino)-phosphoniumhexafluorophosphate (BOP), triethylarnine, methylene chloride)]. The chloro substituent of 5 is then replaced with the desired Q-Y group by palladium catalyzed coupling chemistry (for acetylene coupling see Sakamoto et al., *Chem. Pharm. Bull.*, 1984, 32, 4666–4669; for boronic acid coupling see Finch et al., *J. Chem. Soc. Perkin I*, 1994, 9, 1193–1203). In this way, the use of substituted acetylenes (2-pyridylacetylene) and boronic acid derivatives (2-phenylphenylboronic acid) are added to the C-2 position of the quinoline ring. The amide alcohol 2 may be purified by silica chromatography. Oxidation of 2 (the Dess-Martin reagent in methylene chloride is prefered, but not limiting) affords the aldehyde 3. This procedure can be repeated with a wide variety of amino alcohol derivatives. Those derived from the naturally occurring amino acids are preferred.

Compounds of Formula I wherein variations at the C-2 quinoline substituent, in addition to the method described in Scheme 2, are described in Scheme 3.

Scheme 3

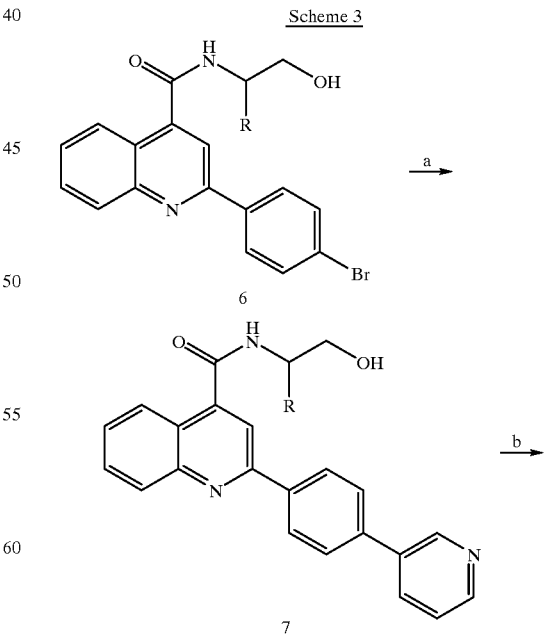

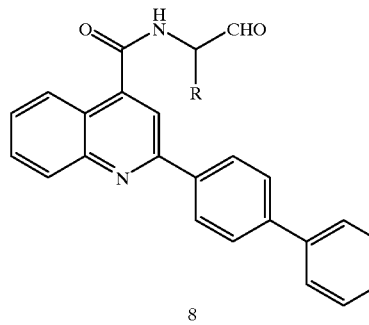

8 a) pyridine-3-tributyltin, Pd(Ph₃P)₄, toluene, 60° C.;
b) Dess Martin reagent, CH₂Cl₂

Compound 6 is prepared according to the boronic acid coupling method described in Scheme 2. Tin mediated coupling of 6 provides the amide alcohol 7 which on oxidation (preferably with Dess-Martin reagent) provides the aldehyde 8.

Additional variation at C-2 of the quinoline ring is accomplished as demonstrated in Scheme 4.

Scheme 4

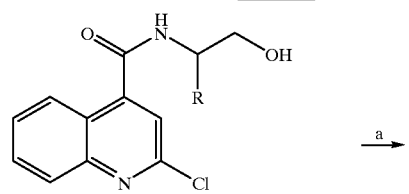

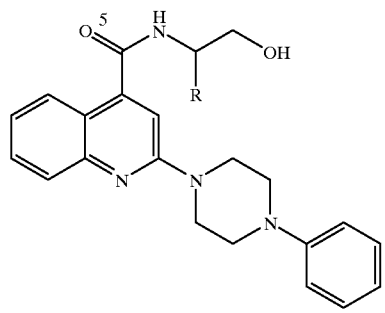

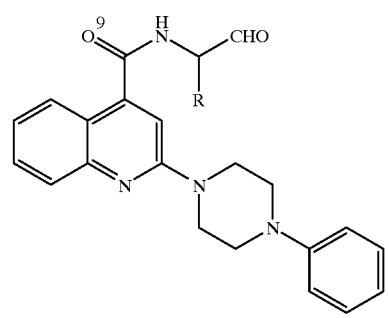

10 a) N-phenylpiperazine, 100° C., 20 hr.;
b) Dess-Martin reagent, CH₂Cl₂

5 is obtained as described in Scheme 2. Treatment with a nucleophilic compound such as N-phenylpiperazine provides the amide alcohol 9 which is conerted into the aldehyde 10 on oxidation (preferably with the Dess-Martin reagent). This method is versatile in that a wide variety of amines and other nucleophilic species can be used to displace the quinoline C-2 chloro group.

Variation of the side chain is accomplished using the functionality of amino acid side chains as demonstrated in Scheme 5.

Scheme 5

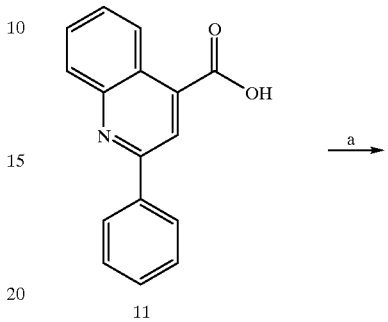

11

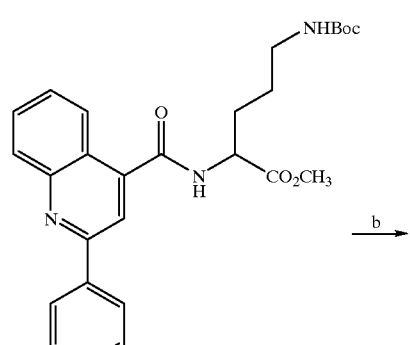

12

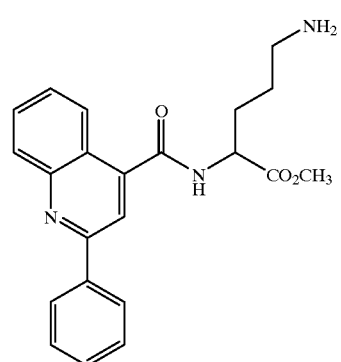

13

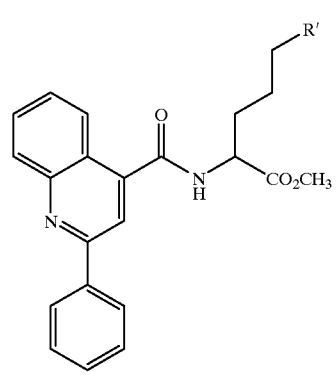

14

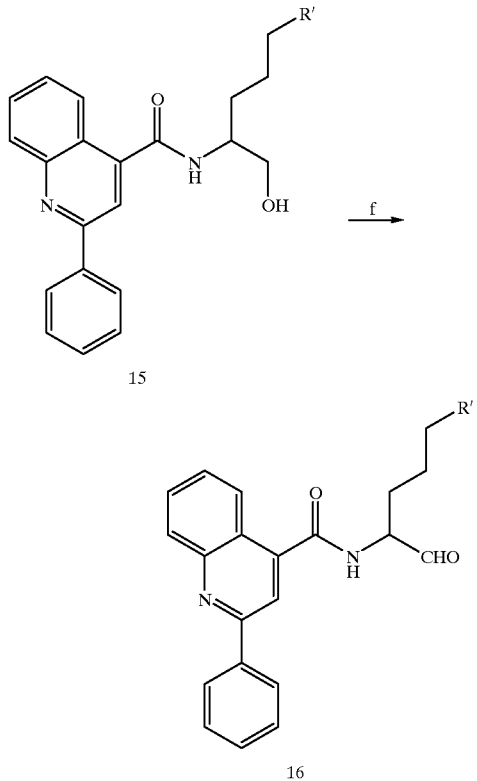

15

16

R' = NHSO$_2$Ph or NCO(intermediate) or NHCOOCH$_2$(4-pyridyl)

a) (L)-H-(Boc)-Lysine-methyl ester hydrochloride, BOP, triethylamine, CH$_2$Cl$_2$;
b) HCl, dioxane, 0° C.;
c) phenylsulfonyl chloride, N-methylmorpholine, THF, 0° C. to ambient temperature;
d) (1) phosgene, pyridine, CH$_2$Cl$_2$; (2) 4-pyridinecarbinol, toluene, reflux;
e) LiBH$_4$, THF, ambient temperature;
f) Dess-Martin reagent, CH$_2$Cl$_2$ Compound 12 is obtained by BOP coupling as previously described (e.g., Scheme 1). Removal of the BOC protecting group using acidic conditions affords 13. The amino group can be reacted in different ways to afford a diversity of products. For example, reacting with a sulfonyl chloride such as phenylsulfonyl chloride affords 14, which upon reduction to 15 (R' is C$_6$H$_5$SO$_2$NH) followed by oxidation provides the desired product 16 (R' is C$_6$H$_5$SO$_2$NH). Alternatively, the amino group of 13 can be converted into an intermediate isocyanate group (phosgene, pyridine, CH$_2$Cl$_2$) such as 14 (R' is —N=C=O) which upon reaction with an appropriate nucleophilic substrate such as an alcohol (HOR), an amine or a mercaptan, affords the corresponding product 14 (R'=—NHCOOR). In such a reaction, treatment of 14 (R' is —N=C=O) with 4-pyridinecarbinol produces 14 (R' is —NHCOOCH$_2$-4-pyridine). Reduction of the ester affords 15 (R' is —NHCOOCH$_2$-4-pyridine) and oxidation provides the desired product 16 (R' is —NHCOOCH$_2$-4-pyridine).

Although these methods illustrate the preparation of compounds for which Z=CHO, alternative "enzyme reactive groups" can be substituted as has been extensively described in the literature (*J. Med. Chem.*, 1994, 37, 2918–2929, *J. Med. Chem.*, 1993, 36, 3472–3480, *J. Med. Chem.* 1990, 33, 11–13, *Biochem. J.*, 1986, 239, 633–640, *J. Med. Chem.*, 1992, 35, 216–220). In addition, these methods are not intended to limit the scope of the possible R groups which can be readily derived from any amino alcohol or amino acid by methods well known in the art.

Also included in the scope of the present invention are pharmaceutically acceptable salts of the compounds of Formula I. Preferred salts include, but are not limited to, hydrochloride, hydrobromide, citrate, tartrate, malate, maleate, lactate, glucose, 1,6-diphosphate, phosphate, succinate, sulfate, aspartate, adipate, methanesulfonate, lauryl sulfate, diguaiacyl phosphate, diacetyl sulfate, glutamate, edetate, ethylene diamine, sodium, potassium, calcium and ethanolamine salts. Such salts are prepared according to standard procedures well known in the art.

The pharmaceutical activity of the compounds of this invention is demonstrated by inhibition of calpain in vitro by the assay procedure described by Sasaki et al., *J. Biol. Chem.* 1984, 259, 12489–12494. The assays were performed using synthetic fluorogenic substrates. Inhibition of enzyme activity was calculated on the percent decease in the rate of substrate hydrolysis in the presence of inhibitor relative to the rate in its absence. IC$_{50}$s(nM) were calculated. Table 1 demonstrates the results of testing representative compounds of Formula I.

TABLE 1

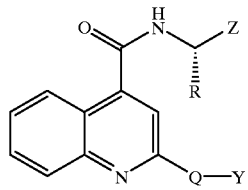

| Z | R | Q-Y | IC$_{50}$(mM) |
|---|---|---|---|
| CHO | CH$_2$Ph | Ph | 65 |
| CHO | CH$_2$Ph | Ph-4-Cl | 66 |
| CHO | CH$_2$Ph | Ph-4-Ph | 20 |
| CHO | CH$_2$Ph | 1-adamantyl | 123 |
| CHO | CH$_2$Ph | Ph-4-OPh | 32 |
| CHO | CH$_2$Ph | Ph-2-Ph | 19 |

TABLE 1-continued

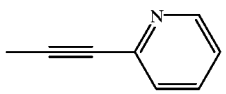

| Z | R | Q-Y | IC$_{50}$(mM) |
|---|---|---|---|
| CHO | CH$_2$Ph | 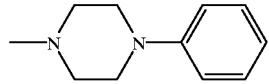 | 16 |
| CHO | CH$_2$Ph | 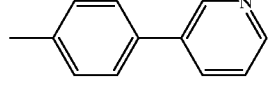 | 38 |
| CHO | CH$_2$Ph | 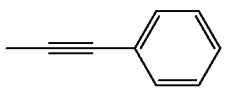 | 46 |
| CHO | (CH$_2$)$_3$CH$_2$NHSO$_2$Ph | Ph | 42 |
| CHO | (CH$_2$)$_3$CH$_2$NHCO$_2$CH$_2$-4-pyridyl | Ph | 160 |
| CHO | CH$_2$Ph | 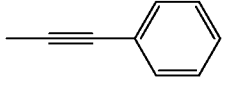 | 12 |
| COCONHn-Bu | CH$_2$Ph | 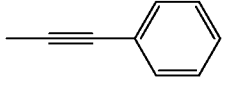 | 77 |

The above results clearly indicate that all compounds tested exhibited significant inhibition of calpain.

The pharmaceutical compositions of this invention employed to inhibit calpain comprise a pharmaceutical carrier and as the active ingredient a compound of Formula I. The active ingredient will be present in the compositions of this invention in an effective amount to inhibit calpain. Preferably, the compositions contain the active ingredient of Formula I in an amount of from about 0.1 mg to about 250 mg, advantageously from about 25 mg to about 150 mg per dosage unit.

The pharmaceutical carrier may be, for example, a solid or liquid. Exemplary of solid carriers are lactose, magnesium stearate, sucrose, talc, stearic acid, gelatin, agar or acacia. Exemplary of liquid carriers are syrups, peanut oil, olive oil, propylene glycol, polyethylene glycol and water.

A wide variety of pharmaceutical forms may be employed. Thus, if a solid carrier is used, the preparation can be tabletted or placed in a hard gelatin capsule. If a liquid carrier is used, the preparation may be in the form of a soft gelatin capsule, placed in an ampule, a liquid suspension, syrup or suspension.

Preferably, parenteral solutions or suspensions are employed. They comprise the active compound in a sterile aqueous or oil carrier such as, for example, peanut oil, polyethylene glycol or polyvinyl pyrolidone. Preferably, such solutions contain the active compound in the range of 0.1 to 140 mg/kg of body weight of the patient to whom it will be administered. The sterile parenteral solutions may also contain additives such as, for example, preservatives such as benzyl alcohol and buffering agents to bring the injectable preparation to a satisfactory pH. Stabilizing agents such as ascorbic acid or sodium bisulfate may also be employed. DMSO or alcoholic solvents may be used to aid in the solubility and penetration of the calpain inhibitor.

The sterile aqueous solutions can also be lyophilized and reconstituted prior to administration.

The parenteral solution may be administered subcutaneously, intravenously, intramuscularly, interperitoneally, intrastemally or by intrathecal injection directly into the central nervous system.

The pharmaceutical compositions are prepared by conventional techniques involving procedures such as mixing, granulating and compressing to dissolve the ingredients as appropriate to the desired preparation.

The method of inhibiting calpain according to this invention comprises administering to an animal or human in an amount sufficient to inhibit calpain a compound of Formula I.

Preferably the compounds of Formula I are administered in conventional dosage unit forms prepared by combining an appropriate dose of the compound with standard pharmaceutical carriers.

Most preferably, the active ingredients of Formula I will be administered in a daily dosage regimen of from about 2.0 mg to about 1.0 g, most preferably from about 50 mg to about 400 mg. Advantageously, equal doses will be administered two to four times a day. When the administration is carried out as described above, inhibition of calpain is produced.

The route of administration of the pharmaceutical compositions of this invention and in accordance with the methods of this invention is internal, more specifically either oral or preferably parenteral, in an amount sufficient to produce the desired biological activity.

The following examples are not limiting but are illustrative of the compounds and compositions of this invention and the process for their preparation.

EXAMPLE 1

Preparation of (S)-N-(1-formyl-2-phenylethyl)-2-phenyl-4-quinolinecarboxamide (a) (S)-N-(1-Hydroxymethyl-2-phenylethyl)-2-phenyl-4-quinoline-carboxamide To a solution of 2-phenyl-4-quinoline-carboxylic acid (0.33 g, 1.3 mmol, Aldrich Chemical Company) in methylene chloride (5 mL) was added benzotriazol-1-yloxytris-(dimethyamino)phosphoniumhexafluorophosphate (BOP) (0.63 g, 1.43 mmol). The resulting mixture was shaken at room temperature for 5 min. (S)-(-)-2-arnino-3-phenyl-1-propanol (0.2 g, 1.3 mmol) was added along with triethylamine (0.2 mL, 1.43 mmol). The resulting mixture was shaken at room temperature for 24 h. Methylene chloride (10 mL) was added and the organic layer was washed with $NaHCO_3$, $H_2O$, brine, dried ($MgSO_4$), filtered, and concentrated in vacuo to give an oil. The oil was purified by flash chromatography (silica gel, 30–80% EtOAc/hexane) to yield the title compound as a white solid (0.3 g, 60%). MS (ES+) m/e 383.5 $[M+H]^+$, 405 $[M+Na]^+$, 787 $[2M+Na]^+$.

(b) (S)-N-(1-Formyl-2-phenylethyl)-2-phenyl-4-quinolinecarboxamide

To a solution of the compound of Example 1(a) (0.1 g, 0.26 mmol) dissolved in methylene chloride (5 mL) was added 1,1,1-triacetoxy-1,1-dihydro-1,2-benziodoxol-3(1H)-one (Dess-Martin periodinane) (0.12 g, 0.3 mmol). The resulting mixture was shaken at room temperature for 1 hr. Sodium thiosulfate solution (10%) (2 mL) was added and the mixture was shaken for 10 min. The organic layer was washed with $NaHCO_3$, brine, dried ($MgSO_4$), filtered, and concentrated in vacuo to give a tan solid. The solid was recrystallized from diethyl ether to yield the title compound as a pale white solid (0.053 g, 54%). $^1$H NMR (400 MHz, $CDCl_3$) δ 9.83 (s, 1H), 8.09 (m, 3H), 7.78 (m, 2H), 7.57 (m, 4H), 7.31 (m, 6H), 6.6 (d, 1H), 5.15 (t, 1H), 3.5 (d, 2H). MS (ES+) m/e 381.4 $[M+H]^+$, 413.4 $[M+H+CH_3OH]^+$.

EXAMPLE 2

Preparation of (S)-2-(4-Chlorophenyl)-N-(1-formyl-2-phenylethyl)-4-quinolinecarboxamide Following the procedures of Examples 1(a), and 1(b) except substituting 2-phenyl-4-quinoline-carboxylic acid with 2-(4-chlorophenyl)-4-quinoline-carboxylic acid, the title compound was prepared as a cream solid (0.06 g, 50% for two steps). MS (ES+) m/e 415 $[M+H]^+$.

EXAMPLE 3

Preparation of (S)-2-[1.1'-Biphenyl]-4-yl-N-(1-formyl-2-phenylethyl)-4-quinolinecarboxamide Following the procedures of Examples 1(a), and 1(b) except substituting 2-phenyl-4-quinoline-carboxylic acid with 2-[1,1'-biphenyl]-4-quinoline-carboxylic acid, the title compound was prepared as a yellow solid (0.07 g, 55% for two steps). MS (ES+) m/e 457 $[M+H]^+$.

EXAMPLE 4

Preparation of (S)-2-(1-Adamantyl)-N-(1-formyl-2-phenylethyl)-4-quinolinecarboxamide Following the procedures of Examples 1(a), and 1(b) except substituting 2-phenyl-4-quinoline-carboxylic acid with 2-(1-adamantyl)-4-quinoline-carboxylic acid, the title compound was prepared as a white solid (0.06 g, 50% for two steps). MS (ES+) m/e 439 $[M+H]^+$, 471 $[M+H+CH_3OH]^+$.

EXAMPLE 5

Preparation of (S)-N-(1-Formyl-2-phenylethyl)-2-(4-phenoxyphenyl)-4-quinolinecarboxamide (a) (S)-N-([1-Hydroxymethyl-2-phenylethyl)-2-chloro-4-quinolinecarboxamide Following the procedure of Example 1(a) except substituting 2-phenyl-4-quinolinecarboxylic acid with 2-chloro-4quinoline-carboxylic acid, the title compound was prepared as a white solid (0.06 g, 70%). MS (ES+) m/e 341 $[M+H]^+$.

(b) (S)-N-(1-Hydroxymethyl-2-phenylethyl)-2-(4-phenoxyphenyl)-4-quinoline-carboxamide To a solution of the compound of Example 5(a) (0.15 g, 0.44 mmol) in dry toluene (4 mL) under argon atmosphere was added tetrakis(triphenylphosphine)-palladium(0) (25 mg, 0.022 mmol) followed by 4-phenoxyphenylboronic acid (0.18 g, 0.88 mmol; Sigma Chemical Company), sodium carbonate (2M solution in $H_2O$, 0.6 mL) and ethanol (2 mL). The resulting mixture was refluxed for 4 h. Methylene chloride (50 mL) was added and the organic layer was washed with $H_2O$, brine, dried ($MgSO_4$), filtered, and concentrated in vacuo to give a solid. The resulting crude yellow solid was triturated with methylene chloride (40 mL, and filtered to yield the title compound as an off-white solid (0.15 g, 75%). MS (ES+) m/e 475 $[M+H]^+$.

(c) (S)-N-(1-Formyl-2-phenylethyl)-2-(4-phenoxyphenyl)4-quinolinecarboxamide

Following the procedure of Example 1(b) except substituting the compound of Example 1(a) with the compound of Example 5(b), the title compound was prepared as a light yellow solid (0.1 g, 73%). MS (ES+) m/e 473 $[M+H]^+$.

EXAMPLE 6

Preparation of (S)-2-[1.1'-Biphenyl]-2-yl-N-(1-formyl-2-phenylethyl)-4-quinolinecarboxamide (a) (S)-2-[1,1'-Biphenyl]-2-yl-N-(1-hydroxymethyl-2-phenylethyl)-4-quinoline-carboxamide To a solution of the compound of Example 5(a) (0.15 g, 0.44 mmol) in dry toluene (4 mL) under argon atmosphere was added tetrakis(triphenylphosphine)-palladium(0) (25 mg, 0.022 mmol) followed by (2-phenyl)phenylboronic acid (0.18 g, 0.88 mmol; synthesized according to the procedure of Kelly et al., *J. Amer. Chem. Soc.*, 1990, 112, 8024–8034), sodium carbonate (2M solution in H$_2$O, 0.6 mL) and ethanol (2 mL). The resulting miture was refluxed for 4 h. Methylene chloride (50 mL) was added and the organic layer was washed with H$_2$O, brine, dried (MgSO$_4$), filtered, and concentrated in vacuo to give a foam. The foam was purified by flash chromatography (silica gel, 25–50% EtOAc/hexane) to yield the title compound as a glassy foam (0.11 g, 59%). MS (ES+) m/e 459.3 [M+H]$^+$.

(b) (S)-2-[1,1'-Biphenyl]-2-yl-N-(1-formyl-2-phenylethyl)-4-quinolinecarboxamide Following the procedure of Example 1(b) except substituting the compound of Example 1(a) with the compound of Example 6(a), the title compound was prepared as an off-white solid (0.045 g, 55%). MS (ES+) m/e 457.2 [M+H]$^+$.

EXAMPLE 7

Preparation of (S)-N-(1-Formyl-2-phenylethyl)-2-(2-pyridinylethynyl)-4-guinolinecarboxamide (a) (S)-N-(1-Hydroxymethyl-2-phenylethyl)-2-(2-pyridinylethynyl]-4-quinoline-carboxamide To a solution of the compound of Example 5(a) (1 g, 2.94 mmol) in dry DMSO (13 mL) under argon atmosphere was added 2-ethynyl pyridine (0.45 g, 4.41 mmol; ICN Chemical Company), diphenylphosphine palladium dichloride (41 mg, 0.059 mmol), copper iodide (22 mg, 0.11 mmol), followed by triethylamine (0.82 mL, 5.88 mmol). The resulting mixture was heated at 60° C. for 4 h. Methylene chloride (50 mL) was added and the organic layer was washed with H$_2$O, brine, dried (MgSO$_4$), filtered, and concentrated in vacuo to give an amber oil. The resulting crude oil was triturated with methylene chloride (40 mL) and methanol (40 mL) and filtered to yield the title compound as an off-white solid (0.4 g, 33%). MS (ES+) m/e 408.2 [M+H]$^+$.

b) (S)-N-(1-Formyl-2-phenylethyl)-2-(2-pyridinylethynyl)-4-quinolinecarboxamide

Following the procedure of Example 1(b) except substituting the compound of Example 1(a) with the compound of Example 7(a), the title compound was prepared as a white solid (0.13 g, 40%). MS (ES+) m/e 406.2 [M+H]$^+$.

EXAMPLE 8

Preparation of (S)-N-(1-Formyl-2-phenylethyl)-2-(4-phenyl-1-piperazinyl)-4-quinolinecarboxamide (a) (S)-N-(1-Hydroxymethyl-2-phenylethyl)-2-(4-phenyl-1-piperazinyl)-4-quinolinecarboxamide The compound of Example 5(a) (0.1 g, 0.29 mmol) was dissolved in 1-phenyl-piperazine (1 mL, 6.5 mmol). The resulting mixture was heated at 100° C. for 24 h. Methylene chloride (50 mL) was added and the organic layer was washed with 1N citric acid, saturated NaHCO$_3$, H$_2$O, brine, dried (MgSO$_4$), filtered, and concentrated in vacuo to give an amber oil. The oil was purified by flash chromatography (silica gel, 25–70% EtOAc/hexane) to yield the title compound as a golden yellow solid (0.03 g, 30%). MS (ES+) m/e 467.4 [M+H]$^+$.

b) (S)-N-(1-Formyl-2-phenylethyl)-2-(4-phenyl-1-piperazinyl)-4-quinolinecarboxamide Following the procedure of Exampie 1(b) except substituting the compound of Example 1(a) with the compound of Example 8(a), the title compound was prepared as a light yellow solid (0.13 g, 40%). MS (ES+) m/e 465.3 [M+H]$^+$.

EXAMPLE 9

Preparation of (S)-N-(1-Formyl2-phenylethyl)-2-[4-(3-pyridinyl)phenyl]-4-quinolinecarboxamide (a) (S)-N-(1-Hydroxymethyl-2-phenylethyl)-2-(4-bromophenyl)4quinolinecarboxamide To a solution of tris(dibenzylideneacetone)dipalladium (0)-chloroform adduct (18 mg, 3 mol %) in toluene (4 mL) under argon atmosphere was added triphenylphosphine (19 mg; 1 mol %). The resulting mixture was stirred at room temperature for 10 min. To the resulting mixture were added the compound of Example 5(a) (0.2 g, 0.58 mmol), 4-bromophenylboronic acid (0.14 g, 0.7 mmol; Lancaster Chemical Company), sodium carbonate (2M solution in H$_2$O, 0.6 mL) and ethanol (0.2 mL). The resulting mixture was heated at 90° C. for 14 h. Methylene chloride (50 mL) was added and the organic layer was washed with H$_2$O, brine, dried (MgSO$_4$), filered, and concentrted in vacuo to give an oil. The oil was purified by flash chromatography (silica gel, 25–70% EtOAc/hexane) to yield the title compound as an oil (0.165 g, 61%). MS (ES+) m/e 461.1 [M+H]$^+$.

(b) (S)-N-(1-Hydroxymethyl-2-phenylethyl)-2-[4-(3-pyridinyl)phenyl]-4-quinoline-carboxamide To a solution of the compound of Example 9(a) (0.16 g; 0.35 mmol) in toluene (10 mL) was added 3-pyridyltributyltin (0.158 g; 0.43 mmol; Maybridge Chemical Company) followed by tetrakis (triphenylphosphine) palladium(0) (44 mg, 12 mol %). The resulting mixture was heated at 60° C. for 15 h. Methylene chloride (50 mL) was added and the organic layer was washed with H$_2$O, brine, dried (MgSO$_4$), filtered, and concentrated in vacuo to give an oil. The oil was purified by flash chromatography (silica gel, 0–15% methanol/CH$_2$Cl$_2$) to yield the title compound as a foam (0.055 g, 30%). MS (ES+) m/e 460.3 [M+H]$^+$.

(c) (S)-N-(1-Formyl-2-phenylethyl)-2-[4-(3-pyridinyl)phenyl]-4-quinolinecarboxamide Following the procedure of Example 1(b) except substituting the compound of Example 1(a) with the compound of Example 9(b), the title compound was prepared as a light yellow solid (0.024 g, 40%). MS (ES+) m/e 458.3 {M+H]$^+$, 490.3 [M+H+CH$_3$OH]$^+$.

EXAMPLE 10

Preparation of (S)-N-[1-Formyl-5-[(phenylsulfonyl) amino]pentyl]-2-phenyl-4-guinolinecarboxamide (a) (S)-N-[1-Carbomethoxy-5-(tetrabutoxyamino]pentyl)]-2-phenyl-4-quinoline-carboxamide To a solution of 2-phenyl-4-quinoline-carboxylic acid (2 g, 8 mmol, Aldrich Chemical Co.) in methylene chloride (10 mL) was added benzotriazol-1-yloxytris-(dimethylamino) phosphoniumhexafluorophosphate (BOP) (3.7 g, 8.4 mmol). The resulting mixture was stirred at room temperature for 5 min. (L)-H-(Boc)-Lysine-methyl ester hydrochloride (2.37 g, 8 mmol) was added along with triethylamine (1.2 mL, 8.6 mmol). The resulting mixture was shaken at room temperature for 24 h. Methylene chloride (50 mL) was added and the organic layer was washed with NaHCO$_3$, H$_2$O, brine, dried (MgSO$_4$), filtered, and concentrated in vacuo to give an oil. The oil was purified by flash chromatography (silica gel, 30–50% EtOAc/hexane) to yield the title compound as a cream solid (3.15 g, 80%). MS (ES+) m/e 492.3 [M+H]$^+$.

(b) (S)-N-(1-Carbomethoxy)-5-aminopentyl-2-phenyl-4-quinolinecarboxamide

To a cooled solution of the compound of Example 10(a) (0.45 g, 0.92 mmol) in dioxane (1 mL) was added a solution of 4N hydrochloric acid in dioxane (2.5 mL). The resulting mixture was stirred at room temperature for 10 min. The mixture was concentrated in vacuo to give an amber oil. The resulting crude oil was triturated with methylene chloride (40 mL) and methanol (40 mL), diethyl ether (40 mL), and filtered to yield the title compound as an off-white solid (0.3 g, 84%). MS (ES+) m/e 392.3 [M+H]$^+$.

(c) (S)-N-(1-Carbomethoxy)-5-[(phenylsulfonyl)amino]pentyl]-2-phenyl-4-quinoline-carboxamide To a cooled solution of the compound of Example 10(b) (0.28 g, 0.6 mmol) in THF (9 mL) under argon atmosphere was added N-methylmorpholine (0.23 mL, 2.1 mmol) followed by phenyl sulfonyl chloride (0.11 mL, 0.9 mmol). The resulting mixture was slowly warmed to room temperature and was stirred at room temperature for 16 h. Ice (10 mL) and H$_2$O (10 mL) were added and the mixture was acidified to pH~3 with 10% aqueous hydrochloric acid. Methylene chloride (50 mL) was added and the organic layer was washed with H$_2$O, brine, dried (MgSO$_4$), filtered, and concentrated in vacuo to give an oil. The oil was purified by flash chromatography (silica gel, 25–60% EtOAc/hexane) to yield the title compound as a glassy foam (0.3 g, 94%). MS (ES+) m/e 532.2 [M+H]$^+$.

(d) (S)-N-(1-Hydroxymethyl)-5-[(phenylsulfonyl)amino]pentyl]-2-phenyl-4quinoline-carboxamide To a cooled solution of the compound of Example 10(c) (0.15 g, 0.28 mmol) in THF (5 mL) under argon atmosphere was added lithium borohydride (0.21 mL, 0.42 mmol; 2M solution in THF). The resulting mixture was stirred at room temperature for 16 h. Methylene chloride (2 mL) was added and the organic layer was washed with 1N citric acid, H$_2$O, brine, dried (MgSO$_4$), filtered, and concentrated in vacuo to give an amber oil. The oil was purified by flash chromatography (silica gel, 50–80% EtOAc/hexane) to yield the title compound as a glassy foam (0.11 g, 83%). MS (ES+) m/e 504.3 [M+H]$^+$.

(e) (S)-N-[1-Formyl-5-[(phenylsulfonyl)amino]pentyl]-2-phenyl-4-quinolinecarboxamide Following the procedure of Example 1 (b) except substituting for the compound of Example 1(a) with the compound of Example 10(d), the title compound was prepared as an off-white solid (0.033 g, 35%). MS (ES+) m/e 502.3 [M+H]$^+$.

EXAMPLE 11

Preparation of (S)-N-(1-Formyl-5-[(4-pyridylmethoxy)carbonylamino]pentyl]-2-phenyl-4-quinolinecarboxamide dihydrochloride salt (a) (S)-N-[1-Carbometboxy-5-isocyanopentyl-2-phenyl-4-quinolinecarboxamide To a cooled solution of the compound of Example 10(b) (1 g, 2.34 mmol) in methylene chloride (10 mL) was added pyridine (0.76 ml, 9.36 mmol) followed by slow addition of phosgene (1.56 mL, 3 mmol; 1.93 M solution in toluene).

The resulting mixture was stirred at 0° C. for 2 h. The resulting mixture was poured into 0.5 N HCl (25 mL) and ice (15 mL). The organic layer was washed with 0.5 N HCl (25 mL) and ice (15 mL). The aqueous layers were extracted with methylene chloride (40 mL) and the combined organic layers were washed with brine, dried (MgSO$_4$), filtered and concentrated to give an oil (0.81 g, 80%) that was used in the next step without purification. MS (ES+) m/e 418.3 [M+H]$^+$.

(b) (S)-N-(1-Carbomethoxy-5-[(4-pyridylmethoxy)carbonylamino]pentyl]-2-phenyl-4-quinolinecarboxamide To a solution of the compound of Example 11 (a) (0.81 g, 1.95 mmol) dissolved in toluene (5 mL) was added 4-pyidine carbinol (0.21 g, 1.95 mmol; Aldrich Chemical Company). The resulting mixture was refluxed for 24 h. Methylene chloride (20 mL) was added and the organic layer was washed with H$_2$O, brine, dried (MgSO$_4$), filtered, and concentrated in vacuo to give an oil. The oil was purified by flash chromatography (silica gel, 0–10% methanol/CH$_2$Cl$_2$) to yield the title compound as a glassy foam (0.46 g, 41%). MS (ES+) m/e 527.3 [M+H]$^+$.

(c) (S)-N-(1-Hydroxymethyl)-5-[(4-pyridylmethoxy)carbonylamino]pentyl]-2-phenyl-4-quinolinecarboxamide Following the procedure of Example 10(d) except substituting for the compound of Example 10(c) with the compound of Example 11(b), the title compound was prepared as an off-white solid (0.14 g, 35%). MS (ES+) m/e 499.3 [M+H]$^+$.

(d) (S)-N-(1-Formyl-5-[(4-pyridylmethoxy)carbonylamino]pentyl]-2-phenyl-4-quinolinecarboxamide dihydrochloride salt Following the procedure of Example 1(b) except substituting for the compound of Example 1(a) with the compound of Example 11(c), the title compound was prepared as a light yellow solid. The solid was dissolved in ethanol (1 mL) and ethereal HCl (2 mL) was added. The precipitated solid was filtered and dried in vacuo to yield the title compound as an off-white solid (0.03 g, 35%). MS (ES+) m/e 497.3 [M+H]$^+$, 529.3 [M+H+CH$_3$OH]$^+$.

EXAMPLE 12

Preparation of (S)-N-(1-formyl-2-(phenylethyl)-2-(phenylethynyl)-4-quinoline-carboxamide (a) (S)-N-(1-hydroxymethyl-2-(phenylethyl)-2-(phenylethynyl)4-quinoline-carboxamide To a solution of the compound of Example 5(a) (4.4 g, 12.9 mmol) in dry DMSO (50 mL) under argon atmosphere was added phenylacetylene (2.13 mL, 19.4 mmol; Aldrich Chemical Company), diphenylphosphine palladium dichloride (181 mg, 2% mol), copper iodide (98 mg, 4% mol), followed by triethylamine (3.6 mL, 25.8 mmol). The resulting mixture was heated at 60° C. for 4 h. Methylene chloride (50 mL) was added and the organic layer was washed with H$_2$O, brine, dried (MgSO$_4$), filtered, and concentrated in vacuo to give an amber oil. The resulting crude oil was triturated with methylene chloride (40 mL) and methanol (40 mL) and filtered to yield the title compound as an off-white solid (4.4 g, 60%). MS (ES+) m/e 407.2 [M+H]$^+$.

(b) (S)-N-(1-formyl-2-(phenylethyl)-2-(phenylethynyl)-4-quinolinecarboxamide

Following the procedure of Example 1(b) except substituting the compound of Example 1(a) with the compound of Example 12(a), the title compound was prepared as a white solid (1.67 g, 50%). MS (ES+) m/e 405.2 [M+H]$^+$.

EXAMPLE 13

Preparation of N-[3-(n-butylamino)-2,3-dioxo-1-(phenylmethyl)]-2-(phenylethynyl)-4-quinolilnecarboxamide (a) (S)-N-(1-formyl-2-phenylethyl)-2-chloro-4-quinolinecarboxamide Following the procedure of Example 1(b) except substituting (S)-N-(1-hydroxymethyl-2-phenylethyl)-2-phenyl-4-quinolinecarboxamide with (S)-N-(1-hydroxymethyl-2-phenylethyl)-2-chloro-4-quinolinecarboxamide, the title compound was prepared as a white solid (1.1 g, 50%). MS (ES+) m/e 339 [M+H]$^+$.

(b) (S)-N-3-[(n-butylamino)-2-hydroxy-3-oxo-1-(phenylmethyl)propyl]-2-(chloro)-4-quinolinecarboxamide To a cooled solution (0° C.) of TiCl$_4$ (1.55 mL, 1.55 mmol; 1M solution in CH$_2$Cl$_2$) in methylene chloride (5 mL) was added n-butyl isocyanide (162 μL, 1.5 mmol). The resulting mixture was stirred at 0° C. for 3 h. The resulting solution was cooled to −78° C. and (S)-N-(1-formyl-2-phenylethyl)-2-chloro-4-quinolinecarboxamide (0.5 g, 1.47 mmol) was added. The resulting mixture was warmed to room temperature over 1 h and stirred at room temperature for 24 h. To the mixture was added 1N HCl (2 mL) and stirred for 30 min. The mixture was diluted with EtOAc and the aqueous layer basified with NaOH and extracted with EtOAc. The combined organic layer was washed with brine and dried over Na$_2$SO$_4$. TLC (40–60 EtOAc:Hexane) showed the disappearance of starting material and appearance of faster and slower running spots. Solvent was removed in vacuo and the resulting mixture was triturated with ether to give the desired compound as precipitated white solid (0.2g, 35%). MS (ES+) m/e 440 [M+H]$^+$.

(c) (S-N-[3-(n-butylamino)-2-hydroxy-3-oxo-1-(phenylmethyl)propyl]-2-(phenyl-ethynyl)-4-quinolinecarboxatuide Following the procedure of Example 12(a) except substituting the compound of Example 5(a) with (S)-N-[3-(n-butylamino)-2-hydroxy-3-oxo-1-(phenylmethyl)propyl]-2-(chloro)4-quinolinecarboxamide, the title compound was prepared as an off-white solid (65 mg, 50%). MS (ES+) m/e 506 [M+H]$^+$.

(d) N-[3-(n-butylamino)-2,3-dioxo-1-(phenylmethyl)]-2-(phenylethynyl)4-quinolinecarboxamide Following the procedure of Example 1(b) except substituting the compound (S)-N-(1-hydroxymethyl-2-phenylethyl)-2-phenyl-4-quinollinecarboxamide with (S)-N-[3-(n-butylamino)-2-hydroxy-3-oxo-1-(phenylmethyl)propyl]-2-(phenylethynyl)-4-quinolinecarboxamide, the title compound was prepared as a white solid (45 mg, 50%). MS (ES+) m/e 504.2 [M+H]$^+$.

EXAMPLE 14

| Ingredients | Mg./Capsule |
|---|---|
| (S)—N-(1-formyl-2-phenylethyl)-2-pyridinyl-ethynyl-4-quinoline-carboxamide | 250.00 |
| Magnesium Stearate | 5.00 |
| Lactose | 100.00 |

The ingredients are thoroughly mixed and filled into a hard gelatin capsule.

EXAMPLE 15

| Ingredients | Mg./Tablet |
|---|---|
| (S)-2-[1,1'-biphenyl]-2-yl-N-(1-formyl-2-phenyl-ethyl)-4-quinolinecarboxamide | 100.00 |
| Lactose | 250.00 |
| Starch | 13.00 |
| Talc | 5.00 |
| Magnesium Stearate | 2.50 |

The lactose and quinolinecarboxamide are mixed and granulated with hot 10% gelatin. The granules are dried and passed through a #20 mesh screen. The granules are then mixed with the starch, talc and magnesium stearate and compressed into a tablet.

One tablet is administered four times a day to mammals for treatment of neurodegenerative diseases.

EXAMPLE 16

| Ingredients | Amounts/Mg. |
|---|---|
| (S)—N-(1-formyl-2-phenylethyl)-2-pyridinyl-ethynyl-4-quinolinecarboxamide | 75.00 |
| DMSO | 500.00 |
| Sodium Chloride | 375.00 |
| Sodium Bisulfite | 100.00 |
| Water for Injection q.s. | 100 ml |

The quinolinecarboxamide is dissolved in the DMSO and 50% of the water. The salts are thoroughly dissolved and the volume is brouht up to 100 ml. The solution is then filtered and filled into ampules and autoclaved.

EXAMPLE 17

| Ingredients | Amounts/Mg. |
|---|---|
| (S)-2-[1,1'-biphenyl]-2-yl-N-(1-formyl-2-phenyl-ethyl)-4-quinolinecarboxamide | 150.00 |
| Peanut Oil | 300.00 |

The ingredients are mixed to a thick slurry and filled into soft gelatin capsules. One capsule is administered orally to mammals for treatment of neurodegenerative diseases.

What is claimed is:

1. A compound of the formula:

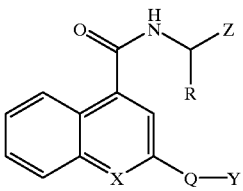

Formula I in which:

X is CH or N;

R is CH$_2$Ph, —(CH$_2$)$_3$CH$_2$NR$_1$R$_3$, CH$_2$CH(CH$_3$)$_2$ or CH$_2$PhOR$_2$;

$R_1$ is $COOCH_2Ph$, $SO_2CH_3$, $SO_2aryl$, $COOCH_{2pyridyl}$ (or substituted pyridyl);
$R_2$ is H, $CH_3$, $CH_2Ph$ or $CH_{2pyridyl}$;
$R_3$ is H, $CH_3$ or lower alkyl;
Z is CHO, $COCH_2F$, COCOOH, COCOOalkyl, COCONHalkyl, $COCO(CH_2)_n aryl$, COCONHCH(R)COOH or $COCH_2O$-3-(phenylisoxazol-5-yl);
n is 1 to 6;

Q is aryl, 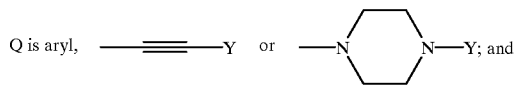

Y=absent, phenyl, substituted phenyl, pyridyl or substituted pyridyl,
or a pharmaceutically acceptable salt thereof.

2. A compound of claim 1 in which the C-5 sterochemistry is S.

3. A compound of claim 2 in which X is N.

4. A compound of claim 3 in which Z is CHO.

5. A compound of claim 4 in which R is $CH_2Ph$ or $—(CH_2)_3CH_2NHR_1$.

6. A compound of claim 5 being (S)-N-(1-formyl-2-phenylethyl)-2-phenyl-4-quinolinecarboxamide.

7. A compound of claim 5 being (S)-2-(4-chlorophenyl-N-(1-formyl-2-phenylethyl)-4-quinolinecarboxamide.

8. A compound of claim 5 being (S)-2-[1,1'-biphenyl]-4-yl-N-(1-formyl-2-phenylethyl)-4-quinolinecarboxamide.

9. A compound of claim 5 being (S)-2-(1-adamantyl)-N-(1-formyl-2-phenylethyl)-4-quinolinecarboxamide.

10. A compound of claim 5 being (S)-N-(1-formyl-2-phenylethyl)-2-(4-phenoxyphenyl-4-quinolinecarboxamide.

11. A compound of claim 5 being (S)-2-[1,1'-biphenyl]-2-yl-N-(1-formyl-2-phenylethyl)-4-quinolinecarboxamide.

12. A compound of claim 5 being (S)-N-(1-formyl-2-phenylethyl)-2-(2-pyridinylethynyl)-4-quinolinecarboxamide.

13. A compound of claim 5 being (S)-N-(1-formyl-2-phenylethyl-2-(4-phenyl-1-piperazinyl)-4-quinolinecarboxamide.

14. A compound of claim 5 being (S)-N-[1-formyl-2-phenylethyl]-2-[(3-pyridinyl)-4-phenyl]-4-quinolinecarboxamide.

15. A compound of claim 5 being (S)-N-[1-formyl-5-[(phenylsulfonyl)amino]-pentyl]-2-phenyl4-quinolinecarboxamide.

16. A compound of claim 5 being (S)-N-[1-formyl-5-[N'-(carbo-4-pyridinemethyloxy)pentyl]-2-[phenyl]-4-quinolinecarboxamide.

17. A compound of claim 5 being (S)-N-(1-formyl-2-(phenylethyl)-2-(phenylethynyl)-4-quinolinecarboxamide.

18. A compound of claim 5 being N-[3-(n-butylamino)-2,3-dioxo-1-(phenylmethyl)]-2-phenylethynyl)-4-quinolinecarboxamide.

19. A pharmaceutical composition in dosage unit form for inhibiting calpain comprising a pharmaceutical carrier and an effective amount of the compound as described in claim 1.

20. A method of inhibiting calpain which comprises administering to an animal or human in an amount sufficient to inhibit calpain a compound as described in claim 1.

21. A method of treating neurodegenerative diseases which comprises administering to an animal or human in need thereof orally or by injection a sufficient amount of a compound of claim 1.

22. The method of claim 20 wherein the amount is from about 50 to about 500 mg of the compound per dosage unit and the administration is orally.

23. The method of claim 20 wherein the amount is from about 0.1 to 140 mg/kg of body weight of the animal or human and the administration is parenterally.

\* \* \* \* \*